United States Patent [19]
Mitchell et al.

[11] Patent Number: 5,684,592
[45] Date of Patent: Nov. 4, 1997

[54] SYSTEM AND METHOD FOR DETECTING ULTRASOUND USING TIME-DELAY INTERFEROMETRY

[75] Inventors: Phillip V. Mitchell, Simi Valley; David M. Pepper; Thomas R. O'Meara, both of Malibu; Marvin B. Klein, Pacific Palisades; Stephen W. McCahon, Newbury; Gilmore J. Dunning, Newbury Park, all of Calif.

[73] Assignee: Hughes Aircraft Company, Los Angeles, Calif.

[21] Appl. No.: 481,673

[22] Filed: Jun. 7, 1995

[51] Int. Cl.$^6$ ............................................. G01B 9/02
[52] U.S. Cl. ............................................. 356/357; 356/351
[58] Field of Search ............................................. 356/357, 358, 356/432, 351; 73/655, 657

[56] References Cited

U.S. PATENT DOCUMENTS

| | | | |
|---|---|---|---|
| 4,046,477 | 9/1977 | Kaule | 356/358 |
| 4,381,676 | 5/1983 | Kaule et al. | 356/358 |
| 4,388,832 | 6/1983 | Kaule | 356/358 |
| 5,131,748 | 7/1992 | Monchalin et al. | 356/349 |
| 5,402,233 | 3/1995 | Schultz et al. | 356/357 |

OTHER PUBLICATIONS

C.B. Scruby and L.E. Drain, "Applications Using Laser Generation of Ultrasound", *Laser Ultrasonics, Techniques and Applications*, Adam Hilger, New York (1990), pp. 325–350.

C.B. Scruby and L.E. Drain, "Radiation Patterns for Laser Ultrasonic Sources", *Laser Ultrasonics, Techniques and Applications*, Adam Hilger, New York (1990), pp. 262–275.

M.P. Petrov et al., "Non-steady-state photo-electromotive-force induced by dynamic gratings in partially compensated photoconductors", *Journal of Applied Physics*, vol. 68 No. 5, (1990), pp. 2216–2225.

S.I. Stepanov et al., "Measuring vibration amplitudes in the picometer GaAs:Cr", *Optics Letters*, vol. 15, No. 21, (1990), pp. 1239–1241.

*Primary Examiner*—Samuel A. Turner
*Attorney, Agent, or Firm*—V. D. Duraiswamy; W. K. Denson-Low

[57] ABSTRACT

An ultrasound detection system that is relatively insensitive to rough workpiece surfaces, suppresses low frequency noise, and provides high sensitivity without the need for active stabilization. An optical probe beam is reflected and phase modulated by a workpiece surface that is being vibrated by ultrasound. A time-delay interferometer optically interferes the phase modulated probe beam with a time-delayed replica of itself. The optical interference generates optical interference fringes that move in accordance with the workpiece surface velocity. The interference fringes are detected by a non-steady-state photo-electromotive-force (NSS-photo-EMF) detector that generates an output signal when the frequency of fringe motion exceeds a predetermined threshold.

25 Claims, 2 Drawing Sheets

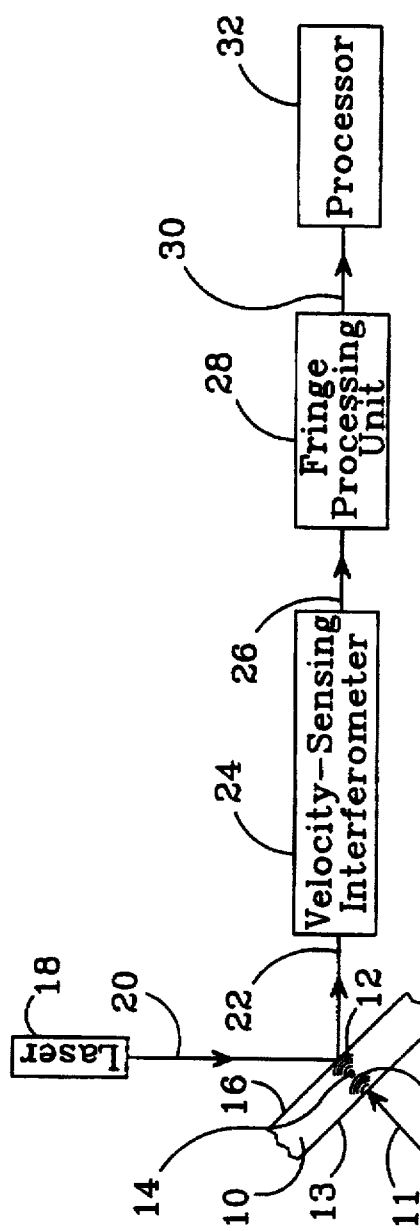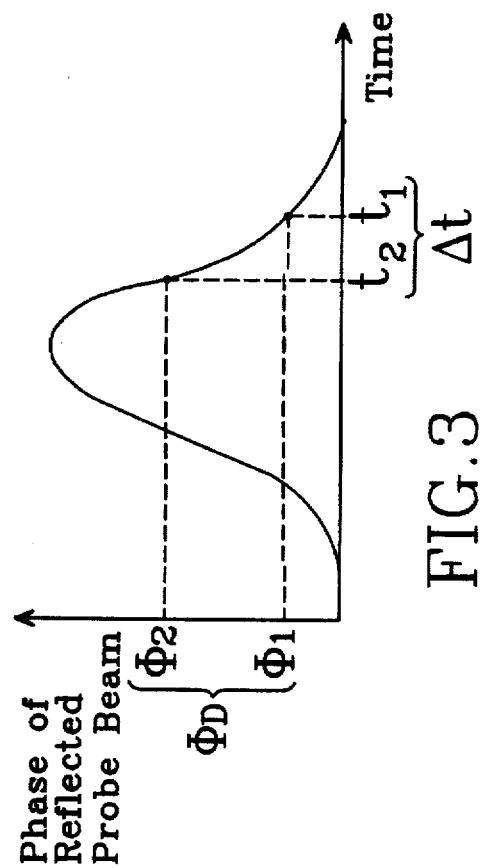

SYSTEM AND METHOD FOR DETECTING ULTRASOUND USING TIME-DELAY INTERFEROMETRY

BACKGROUND OF THE INVENTION

1. Field of the Invention

The present application is related to ultrasonic wave detection and more specifically to laser-based ultrasonic wave detection systems.

2. Description of the Related Art

Ultrasonic waves are commonly used to probe a variety of materials, particularly for thickness gauging and flaw detection. The sound waves are usually generated with a contact piezoelectric transducer. The launched waves propagate through the material, reflecting from interfaces (in thickness gauging applications) or internal features (in flaw detection applications). The scattered sound propagates back to the surface of the workpiece, causing the surface to be displaced with the frequency of the ultrasound. This displacement is usually detected with a contact piezoelectric transducer similar to the one used to generate the sound.

Optical detection techniques, such as those described in C. B. Scruby and L. E. Drain, *Laser Ultrasonics, Techniques and Applications*, Adam Hilger, New York (1990), pages 325-350, can be used in place of the piezoelectric transducers to remotely detect the displacements at the surface of the workpiece. Generally, a laser beam is used to illuminate the surface of the workpiece. When the surface vibrates, it imparts a phase shift on to the reflected beam. This phase shift is detected with a photodetector by mixing the reflected beam with a stable reference beam and measuring the amplitude and frequency of the intensity fluctuations. The reference beam originates from the same laser source as the reflected beam. The output signal from the photodetector corresponds to the surface motion.

One problem associated with laser detection systems is the presence of extraneous mechanical noise sources which cause additional low frequency vibrations at the surface. These additional vibrations are picked up by the reflected laser beam and reduce the signal-to-noise ratio of the system.

Another problem associated with optical systems is low sensitivity. Typically, the surface of the workpiece that is being probed has a diffusely reflecting or scattering quality. Consequently, the reflected beam is highly aberrated and its wavefront is mismatched with respect to the reference beam. The aberrated reflected beam produces a "speckle" field distribution on the optical detector that is used to detect the optical interference between the reflected beam and the reference beam. The phase relationship of the reflected beam to the reference beam is only maintained over a single "speckle" diameter. Consequently, the phase relationship between the reference and reflected beam can be set optimally only for light within the speckle area. Light within other speckles will have a different and generally nonoptimal phase relationship with the reference beam. Consequently, the resulting detector signal can be thousands of times weaker, due to multiple speckle capture, than would be the case if the surface were a perfect mirror (in which all light would be in a single speckle).

One prior laser based ultrasonic detection system, described in U.S. Pat. No. 5,131,748, entitled "BROADBAND OPTICAL DETECTION OF TRANSIENT MOTION FROM A SCATTERING SURFACE BY TWO-WAVE MIXING IN A PHOTOREFRACTIVE CRYSTAL", issued Jul. 21, 1992 to Jean-Pierre Monchalin, et. al., addresses the wavefront matching problem. In this system, a laser beam is reflected from a vibrating surface of a workpiece, which imparts a phase shift onto the reflected beam that corresponds to the amplitude and frequency of the surface vibration. The reflected beam is caused to optically interfere inside a photorefractive crystal with a "pump" beam that is derived from the same laser as the reflected beam. The two beams write an index of refraction grating inside the crystal that diffracts the pump beam in the propagation direction of the reflected beam. When the diffracted pump beam and the reflected beam exit the crystal, they are overlapping and have substantially matching wavefronts. However, the index grating matches the phases of the diffracted pump beam and the reflected beam.

In interferometry the sensitivity of the system is maximized by holding the system in quadrature, which is accomplished by biasing the two interfering beams so that they have a $\pi/2$ phase shift between them. Since the phases of the two interfering beams in the Monchalin system are matched, its sensitivity to the small phase perturbations imparted to the reflected beam by the surface vibrations is very small. To overcome this problem, a second frequency shifted pump beam is superimposed onto the first pump beam. The second pump beam is close enough in frequency to the first pump beam to be Bragg matched to the index grating and, therefore, diffracts off this grating. A second index grating is not written by the second pump beam and the reflected beam because the crystal cannot respond fast enough to the moving fringe grating produced between the beams (the frequency shift between the beams results in non-stationary fringes). As a result, the second pump beam only diffracts off the first stationary grating (written by the first pump beam and the reflected beam) and the relative phase between it and the reflected beam is preserved.

Although this technique improves the system's sensitivity, it suffers from many limitations. First, the second pump beam has to be Bragg matched to the stationary grating written by the first pump beam and the reflected beam. As a result one cannot impart the frequency shifts needed to operate the system in a heterodyne mode. Second, although the wavefronts of the reflected beam and the diffracted pump beam are matched, they are matched to the aberrated wavefront of the reflected beam rather than to the clean wavefront of the pump beam. For example, if the reflected beam is highly diverging, the diffracted pump will likewise be highly diverging. This could lower the amount of light available to the optical detectors in the system. Third, if the surface of the workpiece is de-polarizing (either locally or globally), the sensitivity of the detector goes down. In addition, if the workpiece surface contains highly contrasting features (for example, pits, rust, spots, etc.), the two-wave mixing amplification may result in non-uniform "print-through" (due to pump depletion) which will degrade the system performance. Finally, the Monchalin system does not compensate for extraneous acoustic noise sources which could cause additional vibrations at the surface. These additional vibrations would be detected by the Monchalin system and would lower the signal-to-noise ratio if the amplitude of the noise-induced vibrations are large enough to bias the system out of the linear regime. This occurs if the noise-induced vibrations impart a phase shift on the order of $\pi/2$ radians. In industrial environments large amplitude noise is very common. Therefore, the Monchalin system is not suitable for industrial applications.

An alternative interferometric technique for detecting ultrasound uses a "velocity-sensing" interferometer that produces an output proportional to the velocity, rather than the displacement, of the moving workpiece surface. Time-delay interferometry, described in the Scruby et al. book, pages 123-127, is one such technique. In time-delay interferometry, the probe beam that is reflected from the workpiece surface is split into two interferometer beams and then recombined at a standard photodetector, with one of the beams being time-delayed with respect to the other beam by having it traverse a longer distance. The two beams are colinear when they are recombined at the photodetector. The light intensity at the photodetector is proportional to the velocity of the workpiece surface. Ideally, the reflected readout beam is interfered with a time-delayed replica of itself and the wavefronts of the two interfering beams are substantially matched. Consequently, a phase shift in one leg of the interferometer is common to all speckles, and all speckles can be detected optimally. Unlike a conventional interferometer, which has a flat frequency response to phase shifts, a time-delay interferometer has a band-pass type of response. The time-delay interferometer suppresses both the low frequency (below ultrasonic frequencies), as well as high frequency (above ultrasonic frequencies) vibrations.

Two problems exist with this type of system. First, the speckles are often so plentiful and small as to not be easily alignable with each other after one arm of the interferometer is time-delayed with respect to the other arm. Further, this time delay is most easily accomplished with a multi-mode fiber which further increases the number of speckles and scrambles their locations, making speckle registration impossible. The second problem is that the time delay must be held constant and stabilized in quadrature (required for homodyne detection).

If the path length difference that causes the time delay between the beams is not maintained to within a fraction of a wavelength, the sensitivity of the system will be greatly reduced. As a result, velocity interferometers must typically employ active stabilization techniques. In industrial environments, the frequency range and amplitude of the noise-induced vibrations reduce the effectiveness of active stabilization techniques.

SUMMARY OF THE INVENTION

In view of the above problems, the present invention provides an ultrasonic detection system that is relatively insensitive to rough workpiece surfaces, suppresses low frequency noise, and provides high sensitivity without the need for active stabilization.

This is accomplished by reflecting an optical probe beam from a workpiece surface that is being vibrated by the ultrasound of interest. The reflected probe beam is phase modulated by the ultrasonic vibrations and is directed to the first stage of the system, which comprises a velocity-sensing interferometer. The velocity-sensing interferometer generates optical interference fringes which move in accordance with the velocity of the workpiece surface.

The second stage of the system comprises a fringe processing unit (FPU) that detects the interference fringes and generates an output signal when the frequency of the fringe motion exceeds a predetermined threshold. The third stage of the system comprises a processor that extracts information about the ultrasonic wave from the output signal of the FPU.

The combination of a velocity-sensing interferometer and an FPU that is sensitive to the frequency of the overall fringe pattern motion, rather than the exact shape of the fringe pattern, results in a system that is relatively insensitive to rough workpiece surfaces. In addition, since the FPU is sensitive only to the fringes' frequency of motion rather than their absolute position, the interferometer does not have to be held in quadrature. Slow drifts in the position of the optical fringes due to interferometer instability are not picked up by the FPU, since only frequencies above its threshold are detected. This eliminates the need for active stabilization of the interferometer.

In the preferred embodiment, the velocity-sensing interferometer is implemented with a modified time-delay interferometer that optically interferes the phase modulated probe beam with a time-delayed portion of itself, using a non-zero crossing angle. The optical mixing generates optical interference fringes that move in accordance with the velocity of the workpiece surface.

The FPU is preferably implemented with a non-steady-state photo-electromotive-force (NSS-photo-EMF) detector. The detector is positioned so that the interference fringes are formed directly on it. The detector is made from a photoconductor that forms a space charge grating in response to the alternating light and dark interference fringes. No current flows through the photoconductor as long as its response time is fast enough to allow the space charge grating to track the movement of the interference fringes. If the interference fringes move at a rate that is faster than the space charge grating response time, a net current flows through the conductor. Therefore, the NSS-photo-EMF generates a detector signal when the frequency of fringe motion exceeds a predetermined threshold.

Both the velocity-sensing interferometer and the NSS-photo-EMF detector are frequency band-pass devices. Since the velocity-sensing interferometer supresses the low frequency vibrations without regard to light intensity or vibration ampitude, it can be used as a prefilter to the NSS-photo-EMF detector. This is advantageous because the tracking speed and range of a NSS-photo-EMF detector is intensity dependent and practical laser sources are not always sufficiently intense to guarantee that the detector will track out all the background motion. Consequently, with the velocity-sensitive prefilter, the NSS-photo-EMF detector does not need to supress the low frequency large amplitude background vibrations and the intensity level needed to operate the detector is reduced. Thus, larger standoff distances, low intensity sources and large f-number (inexpensive) optics become practical.

These and other features and advantages of the invention will be apparent to those skilled in the art from the following detailed description of preferred embodiments, taken together with the accompanying drawings, in which:

BRIEF DESCRIPTION OF THE DRAWINGS

FIG. 1 is a block diagram illustrating the basic principles of the invention.

FIG. 3 is a graph illustrating the phase of a reflected probe beam as a function of time.

DETAILED DESCRIPTION OF THE INVENTION

Figure 2:
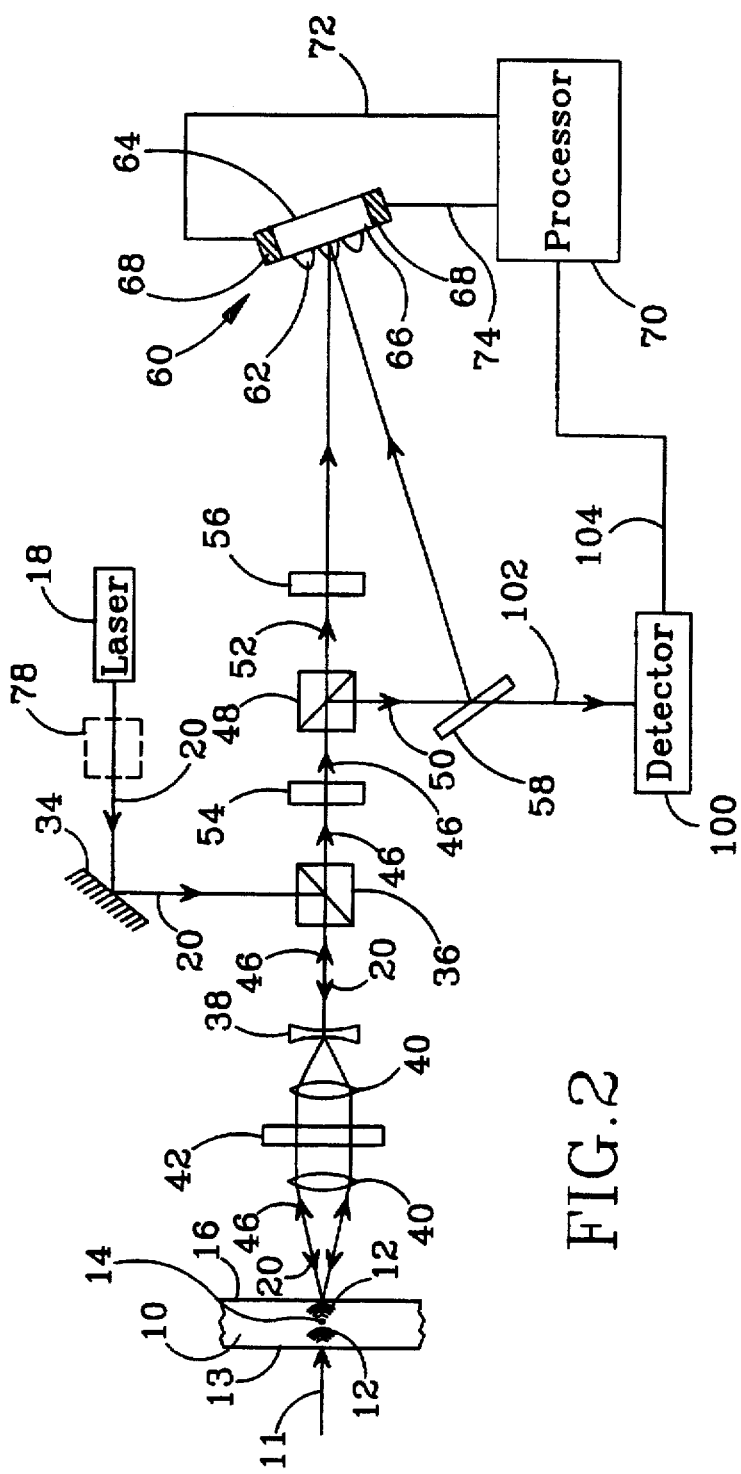
FIG. 2 is a schematic diagram illustrating a preferred embodiment of the invention.

FIG. 1 illustrates the basic principles of the invention. It is assumed that ultrasound is used to characterize a solid workpiece 10. The ultrasound can be self-generated in the workpiece through normal processing, servicing or aging (via acoustic emission). However, more often such ultrasound 12 is generated in the workpiece 10 with a laser beam 11 directed to one side of the workpiece 10. The beam 11 Generates ultrasound through either thermoelastic effects or an ablation of material from the surface 13 of the workpiece 10. For an overview of laser techniques used to Generate ultrasound, see C. B. Scruby and L. E. Drain, *Laser Ultrasonics, Techniques and Applications*, Adam Hilger, New York (1990), pages 262–274. The ultrasound 12 propagates to the readout surface 16, causing the surface to vibrate. If an internal feature 14, such as a weld or crack is present in the workpiece, the amplitude of the ultrasound 12 at the readout surface 16 will be affected. This phenomena can be used to locate the presence and size of an internal feature 14.

A laser 18 generates an optical probe beam 20 that is directed to a portion of the readout surface 16 being vibrated by the ultrasound 12. In some applications (such as weld inspection) the location of the internal feature is known and the probe beam 20 is preferably directed to an area on the readout surface 16 that is directly opposite the internal feature 14.

Upon reflection from the readout surface 16, the probe beam is phase modulated by the vibrations induced on the readout surface 16 by ultrasound 12. The reflected probe beam 22 is then directed to a velocity-sensing interferometer 24, which generates optical intereference fringes (represented schematically by arrow 26) which move in accordance with the velocity of the surface portion.

A fringe processing unit (FPU) 28 detects the interference fringes 26 and generates an output signal 30 when the frequency of the fringe motion exceeds a threshold value. A processor 32 extracts information about the ultrasonic waves 12, and therefore the internal feature 14, from the output signal 30.

FIG. 2 illustrates a preferred embodiment of the invention. A laser 18, preferably a laser that generates a linearly polarized beam, is used to generate a probe beam 20. The type of laser used will depend upon the photoconductor material used in the interferometer signal detector, as will be explained below.

The probe beam 20 is directed by mirror 34 to a beam director 36, preferably a polarizing beamsplitter (PBS), that transmits one polarization component and reflects an orthogonal component. For illustration, the polarization of the probe beam 20 is chosen so that the probe beam is reflected by PBS 36. The probe beam 20 is expanded and collimated by lenses 38 and 40 and passes through a polarization rotator 42, preferably a quarter-wave plate, that converts its linear polarization to circular polarization. A focusing lens 44 focuses the probe beam 20 onto the readout surface 16. As explained above, the probe beam 20 is preferably directed to an area on the readout surface 16 that is directly opposite the internal feature 14 that is being probed. The ultrasound waves 12 are initially established in the workpiece 10 in the same way illustrated in FIG. 1. The focal length of lens 44 is preferably chosen so that the diameter of the probe beam 20 at the readout surface 16 is comparable to or less than the uniform part of the ultrasonically-induced surface vibration (typically 1 mm or less).

Upon reflection from the readout surface 16, the probe beam is phase modulated by the vibrations induced on the readout surface 16 by the ultrasound 12. The readout surface 16 is assumed to be smooth enough so that the reflected probe beam 46 substantially maintains its circular polarization. The reflected probe beam 46 passes back through lenses 44, 40 and 38, and also back through quarter-wave plate 42, which converts its polarization from circular to a linear polarization state that is orthogonal to the probe beam's initial linear polarization state. This allows the reflected probe beam 46 to pass through PBS 36.

A beam divider 48, preferably a PBS, divides the reflected probe beam 46 into interferometer beams 50 and 52. Since PBS 48 transmits one linear polarization state and reflects an orthogonal component, a polarization rotator 54, preferably a half-wave plate, is preferably used to control the relative magnitudes of interferometer beams 50 and 52. Another half-wave plate 56 is used to rotate the polarization of one of the interferometer beams (beam 52 for illustration) so that beams 50 and 52 have substantially the same polarization state.

Mirror 58 directs beam 50 so that beams 50 and 52 overlap and optically interfere at detector 60 and generate optical interference fringes 62. The spatial period of the interference fringes 62 is dependent upon the wavelength of the interferometer beams 50 and 52, and on the angle θ between the two beams. Mirror 58 is preferably positioned so that the lengths of the paths traversed by beams 50 and 52 differ. For illustration, the path of beam 50 has been made longer than the path of beam 52. This results in the reflected probe beam 46 being optically interfered with a time-delayed portion of itself. The time delay, Δt, is determined by the path length difference between beams 50 and 52.

The phase difference ($\phi_D$) between beams 50 and 52 at any given time (t) produced by time delay Δt (and therefore the relative locations of the light and dark regions that make up the interference fringes) is proportional to the distance moved by the readout surface 16 in time Δt as follows:

$$\phi_D(t) = \frac{2\pi}{\lambda} [x(t) - x(t - \Delta t)]$$

where x(t) is the position of the readout surface 16 at time t, and λ is the wavelength of beams 50 and 52. The expression [x(t)−x(t−Δt)] is simply the change in position of readout surface 16 over time Δt. The expression above for $\phi_D$ assumes that the path difference between beams 50 and 52 is equal to an integral number of laser wavelengths. If the path difference is not an integral number of laser wavelengths, an additional constant phase difference would appear on top of the phase difference caused by the surface motion (even with no motion of the workpiece surface). Since this additional phase difference is constant, it does not affect the operation of the system. This effect is better understood by referring to FIG. 3, which is a graph that illustrates the phase of the reflected probe beam 46 as a function of time when the readout surface 16 is being vibrated by ultrasound 12. The reflected probe beam 46 is divided into interferometer beams 50 and 52 that arrive at detector 60 at times $t_1$ and $t_2$, respectively. As a result, beam 50 has phase $\phi_1$ and beam 52 has phase $\phi_2$ at the detector 62. This phase difference determines the relative locations of the light and dark regions that make up the interference fringes 62.

The ultrasound 12 cause an oscillatory movement of the readout surface 16, which results in a phase vs time curve with a non-uniform slope, as illustrated in FIG. 3. When $\phi_D$/Δt changes over time, the interference fringes 62 become non-stationary, with their frequency of motion dependent on the frequency of the oscillatory movement of the workpiece surface caused by the ultrasonic waves. When the ultrasound 12 is comprised of ultrasonic pulses, the path length difference between beams 50 and 52 is preferably made so that time delay Δt is greater than or equal to the full-width-half-maximum of the ultrasonic pulses. When the ultrasound is comprised of fixed frequency ultrasonic waves, the path length difference is preferably made so that time delay Δt is approximately equal to half the period of the ultrasonic waves. These time delays are preferred because it preserves most of the frequency content of the ultrasonic signal while severely supressing ambient and low frequency sound.

Referring back to FIG. 2, the interference fringes are detected by FPU 60, which is preferably an NSS-photo-EMF detector. Various NSS-photo-EMF detectors are described in M. P. Petroy et al., "Non-steady-state photo-electromotive-force induced by dynamic gratings in partially compensated photoconductors", *Journal of Applied Physics*, Vol. 68, No. 5 (1990), pp. 2216–2225; and S. I. Stepanov et al., "Measuring vibration amplitudes in the picometer range using moving light gratings in photoconductive GaAs:Cr", *Optics Letters*, Vol. 15, No. 21 (1990), pp. 1239–1241.

The NSS-photo-EMF detector 60 includes a photorefractive-like photoconductive material 64, preferably a 1 mm thick sample of semi-insulating GaAs:Cr with a front face 66 that has been polished to optical quality and anti-reflection coated. Although GaAs:Cr is preferred, other photoconductors, such as $Bi_{12}SiO_{20}$, CdTe:V, or InP:Fe may also be used. The wavelength of laser 18 should be chosen to maximize the sensitivity of the photoconductor 64. For a GaAs:Cr photoconductor, laser 18 is preferably a GaAs laser that emits light with a wavelength of 900 nm.

Electrodes 68 are ideally fabricated on the sides of the sample that are perpendicular to the front surface 66. The electrodes 68 should be ohmic, providing little voltage drop to the current flow. Practically, these side contacts are expensive. Surface electrode strips are much easier to process and may be preferred when the cost is considered. Alternatively, ohmic contacts could be diffused from the front surface 66 to the back side, thereby providing front side processing with side contacts. Due to the high resistivity of the substrate material 64, silver paint can also be used to provide a simple electrode 68.

In operation, the optical interference fringes 62 are formed on the front surface 66 of the detector 60. Photo-induced carriers (not shown) are created in the illuminated regions of the photoconductor (the regions under the "light" interference fringes). The carriers in the illuminated region of the photoconductor diffuse toward the dark regions of the photoconductor (the regions under the "dark" interference fringes), causing a charge separation that results in the creation of a space-charge "grating" in the photoconductor 64. The period of the space-charge grating is the same as the period of the interference fringes 62.

The carrier diffusion causes a net current flow from the light regions to the dark regions of the photoconductor 64. Once the charge separation reaches equilibrium (which means the space-charge grating is fully formed), these internal currents across the photoconductor 64 go to zero. If fringes 62 move (due to a change in the velocity of the readout surface 16), whether or not current will flow across the photoconductor 64 will depend upon the frequency of the fringe motion. If the frequency is low enough so that the space-charge grating can track the interference fringes then no net current will flow across the photoconductor 64. At a threshold frequency, the space charge grating cannot track the interference fringes and a net current is produced as the newly photoionized carriers respond to the electric field created by the previously formed space charge grating. The threshold fringe motion frequency (and therefore the threshold vibration frequency) is determined by the intrinsic properties (response time) of the photoconductor 64 and the intensity of the laser light. With GaAs:Cr, surface vibration frequencies greater than 10 kilohertz will produce a net current flow across the photoconductor 64. Once the threshold fringe motion frequency is exceeded, the current flow (signal) will be constant with frequency until the upper limit band pass edge is reached (determined by the photoconductor's recombination time limit). A processor 70 monitors the current flow across the photoconductor 64 with electrodes 68 and signal lines 72 and 74. The processor 70 is programmed to extract information about the ultrasonic waves 12 from the magnitude of the current flow across the photoconductor 64. As mentioned above, the presence and size of an internal feature 14 can be determined by monitoring the amplitude of the ultrasound 12 at the readout surface 16. Such amplitude information can be extracted by the processor 70 by monitoring the magnitude of the current flow across the photoconductor 64. However, the present invention is not limited to determining the size and shape of an internal feature. The present detector may be used in any system in which ultrasonic waves are used to vibrate the surface of a workpiece.

In the preferred embodiment, mirror 58 is partially transmitting and an optical detector 100 is used to monitor the transmitted portion 102 of beam 50. In this way, changes in the reflectivity of readout surface 16 are monitored and sent to processor 70 through signal line 104, which uses the information to normalize the output of the NSS-photo-EMF detector 60. This keeps the processor from interpreting a change in signal due to changes in the read-out surface 16 reflectivity as an ultrasonic signal.

The combination of a modified time-delay interferometer and an NSS-photo-EMF detector results in the suppression of low frequency phase noise. This is because a low frequency vibration of the readout surface 16 will result in low frequency motion of the interference fringes 62, which are not detected by the NSS-photo-EMF detector 60 (as long as the fringe motion frequency is lower than the response time of the photoconductor 64). Active stabilization of the interferometer is not required because the interferometer does not have to be held in quadrature. Furthermore, any slow drifts in the interference fringes caused by instability in the interferometer will not be picked up by the detector 60.

For applications in which the absolute value of the ultrasonic wave magnitude must be known, an electro-optic phase shifter 78 may be placed in the probe beam 20 path to impart a known phase shift to the probe beam 20 when no ultrasonic waves are vibrating the readout surface 16. This allows one to continuously calibrate the system.

The present detection system may be used with optically rough readout surfaces 16 because it is generally insensitive to laser "speckle", as explained above. If the readout surface de-polarizes the probe beam 20, the detector signal is reduced by one-half, which is not a problem if the detector exhibits sufficiently high signal-to-noise. The insensitivity to dynamic laser "speckle" and background vibrations make the present system particularly suitable for assembly line inspection systems, in which workpieces are inspected while they are moving at relatively high velocities.

Figure 4:
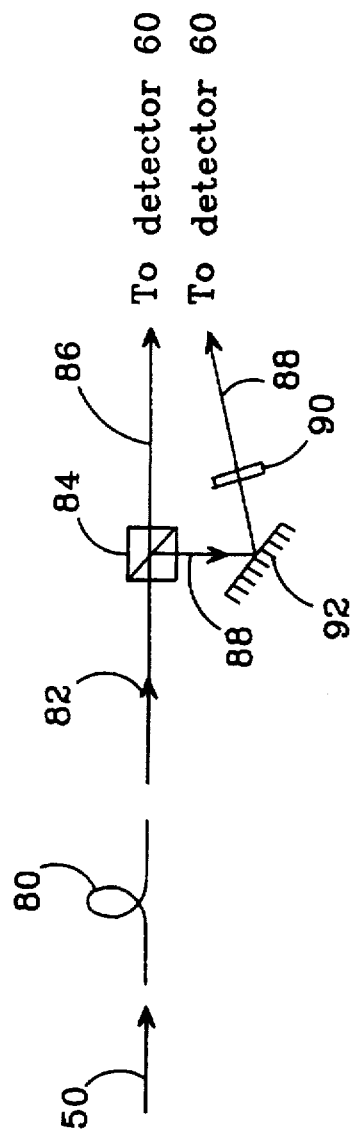
FIG. 4 is a schematic diagram illustrating an alternative configuration for generating a time delay between the interferometer beams used in the embodiment of FIG. 2.

As explained above, the time delay Δt between beams 50 and 52 may be generated by making the path of beam 50 longer than the path of beam 52. However, it may also be generated by passing beam 50 through a material that has a higher index of refraction than air, such as a glass fiber, as illustrated in FIG. 4. In FIG. 4, beam 50 is passed through an optical fiber 80, preferably a multi-mode fiber. The fiber output beam 82 is de-polarized and is passed through a polarizing beamsplitter (PBS) 84 that splits the output beam 82 into orthogonally polarized beams 86 and 88. PBS 84 is preferably oriented so that beam 86 has the same linear polarization as beam 52, and is directed to detector 60. A polarization rotator, preferably a half-wave plate 90 is used to rotate the polarization of beam 88 so that it has the same polarization as beams 52 and 86, and is directed to detector 60 by mirror 92. In this configuration, beams 86 and 88 are preferably directed to different areas of detector 60, and beam 52 is preferably directed so that it overlaps beams 86 and 88.

While several illustrative embodiments of the invention have been shown and described, numerous variations and alternate embodiments will occur to those skilled in the art. For example, any photoconductor which will support space-charge gratings may be used. Such variations and alternate embodiments are contemplated, and can be made without departing from the spirit and scope of the appended claims.

We claim:

1. A detection system for detecting displacement of a workpiece surface, comprising:
   an optical beam generator which generates an optical probe beam and which is arranged so that said probe beam is reflected from said surface and phase modulated by said displacement,
   a velocity-sensing interferometer positioned to receive said reflected and phase-modulated probe beam and configured to generate, in response, interferometer beam that converge at a non-zero angle to form optical interference fringes which have a fringe motion in accordance with the velocity of said surface, and
   a fringe processing unit positioned to receive said interference fringes and configured to generate, in response, and output signal which corresponds to said fringe motion when the frequency of said fringe motion exceeds a predetermined threshold, wherein said fringe processing unit comprises a non-steady-state photo-electromotive-force (NSS-photo-EMF) detector.

2. The detection system of claim 1, wherein said optical beam generator comprises a laser.

3. The detection system of claim 1, wherein said velocity sensing interferometer comprises:
   a beam divider which divides said reflected and phase-modulated probe beam into first and second interferometer beams; and
   a beam director positioned to direct at least one of said interferometer beams so that said interferometer beams overlap at said fringe processing unit and generate said optical interference fringes, said beam director positioned to delay the arrival time of one of said interferometer beams at said fringe processing unit by an amount Δt, thereby causing the phases of said interferometer beams to differ by an amount $\phi_D$ at said fringe processing unit.

4. The detection system of claim 3, wherein said beam director comprises a partially transmitting mirror which reflects a portion of said at least one interferometer beam to said fringe processing unit and transmits another portion, and further comprising:
   an optical detector positioned to detect said transmitted beam portion, and configured to send a normalization signal to said processor, said normalization signal varying as the reflectivity of said surface varies.

5. The detection system of claim 3, wherein said optical beam generator is a polarized beam generator and said optical probe beam has a linear polarization state.

6. The detection system of claim 5, wherein said beam divider comprises:
   a polarizing beamsplitter which transmits one polarization component and reflects an orthogonal polarization component of said reflected and phase-modulated probe beam, said transmitted and reflected components comprising said first and second interferometer beams;
   a first polarization rotator positioned before said polarizing beamsplitter to adjust the polarization state of said reflected and phase-modulated probe beam, thereby adjusting the magnitudes of said first and second interferometer beams; and
   a second polarization rotator positioned after said polarizing beamsplitter to rotate the polarization of one of said interferometer beams so that the polarization state of said interferometer beams are substantially equal when said beams overlap at said fringe processing unit.

7. The detection system of claim 3, wherein said beam director comprises a multimode optical fiber which delays the arrival time of one of said interferometer beams at said fringe processing unit by an amount Δt.

8. The detection system of claim 3, wherein said displacement comprises pulses, and said beam director is positioned so that the value of Δt at said fringe processing unit is greater than or equal to the full-width-half-maximum of said pulses.

9. The detection system of claim 3, wherein said displacement comprises fixed frequency waves, and said beam director is positioned so that the value of Δt at said o fringe processing unit is approximately equal to half the period of said waves.

10. The detection system of claim 1, wherein said optical beam generator is a polarized generator that generates said optical probe beam as a linearly polarized probe beam;
    and further including:
      a polarizing beamsplitter which reflects said linearly polarized probe beam;
      a polarization rotator which receives said linearly polarized probe beam from said polarizing beamsplitter and converts the polarization of said linearly polarized probe beam to circular polarization; and
      a focuser which focuses said circularly polarized probe beam onto said surface and collects said circularly polarized probe beam after phase-modulation and reflection from said surface;
    said polarization rotator being positioned so that said phase modulated and reflected probe beam passes back through said polarization rotator and its polarization is converted to a linear polarization state that is directed through said polarizing beamsplitter to said velocity-sensing interferometer.

11. The detection system of claim 1, wherein said velocity sensing interferometer comprises:
    a beam divider which divides said reflected and phase-modulated probe beam into first and second interferometer beams, and
    a beam director positioned to direct at least one of said interferometer beams so that said interferometer beams overlap at said fringe processing unit and generate said optical interference fringes, said beam director positioned to delay the arrival time of one said interferometer beams at said fringe processing unit by an amount Δt, thereby causing the phases of said interferometer beams to differ by an amount $\phi_D$ at said fringe processing unit.

12. The detection system of claim 11, wherein said optical beam generator is a polarized beam generator and said optical probe beam has a linear polarization state;

and wherein said beam divider includes:

a polarizing beamsplitter which transmits one polarization component and reflects an orthogonal polarization component of said reflected and phase-modulated probe beam, said transmitted and reflected components comprising said first and second interferometer beams;

a first polarization rotator positioned before said polarizing beamsplitter to adjust the polarization state of said reflected and phase-modulated probe beam, thereby adjusting the magnitudes of said first and second interferometer beams; and a second polarization rotator positioned after said polarizing beamsplitter to rotate the polarization of one of said interferometer beams so that the polarization state of said interferometer beams are substantially equal when said beams overlap at said fringe processing unit.

13. The detection system of claim 1, wherein said optical beam generator is a polarized beam generator and said optical probe beam is a linearly polarized probe beam;

and further including:

a polarizing beamsplitter which reflects said linearly polarized probe beam;

a polarization rotator which receives said linearly polarized probe beam from said polarizing beamsplitter and converts the polarization of said linearly polarized probe beam to circular polarization; and a focuser which focuses said circularly polarized probe beam onto said surface and collects said circularly polarized probe beam after phase-modulation and reflection from said surface;

said polarization rotator being positioned so that said phase modulated and reflected probe beam passes back through said polarization rotator and its polarization is converted to a linear polarization state that is directed through said polarizing beamsplitter to said velocity-sensing interferometer.

14. An ultrasonic detector for detecting ultrasound that vibrates a portion of a workpiece surface, comprising:

an optical beam generator for generating an optical probe beam;

a first beam director for focusing and directing said beam to said vibrated surface so that said beam is phase modulated by said vibrations and is reflected off said surface;

a velocity-sensing interferometer for receiving said reflected and phase-modulated probe beam and for generating optical interference fringes which move in accordance with the velocity of said surface portion;

a second beam director for directing said reflected and phase-modulated probe beam to said velocity-sensing interferometer;

a fringe processing unit (FPU) for detecting said and for generating an output signal when the frequency of said fringe motion exceeds a predetermined threshold;

a processor for extracting information about said ultrasonic sound from said output signal; and an electro-optic phase shifter for imparting a calibrating phase shift to said optical probe beam.

15. The detector of claim 14, wherein said velocity sensing interferometer includes:

a beam divider which divides said reflected and phase-modulated probe beam into first and second interferometer beams, and a third beam director positioned to direct at least one of said interferometer beams so that said interferometer beams overlap at said fringe processing unit and generate said optical interference fringes, said third beam director positioned to delay the arrival time of one said interferometer beams at said fringe processing unit by an amount $\Delta t$, thereby causing the phases of said interferometer beams to differ by an amount $\phi_D$ at said fringe processing unit.

16. The detector of claim 15, wherein said beam divider includes:

a polarizing beamsplitter which transmits one polarization component and reflects an orthogonal polarization component of said reflected and phase-modulated probe beam, said transmitted and reflected components comprising said first and second interferometer beams;

a first polarization rotator positioned before said polarizing beamsplitter to adjust the polarization state of said reflected and phase-modulated probe beam, thereby adjusting the magnitudes of said first and second interferometer beams; and a second polarization rotator positioned after said polarizing beamsplitter to rotate the polarization of one of said interferometer beams so that the polarization state of said interferometer beams are substantially equal when said beams overlap at said fringe processing unit.

17. The detector of claim 14, wherein said optical beam generator is a polarized beam generator that generates said optical probe beam as a linearly polarized probe beam and said first beam director includes:

a polarizing beamsplitter which reflects said linearly polarized probe beam;

a polarization rotator which receives said linearly polarized probe beam from said polarizing beamsplitter and converts the polarization of said linearly polarized probe beam to circular polarization; and a focuser which focuses said circularly polarized probe beam onto said surface and collects said circularly polarized probe beam after phase-modulation and reflection from said surface;

said polarization rotator being positioned so that said phase modulated and reflected probe beam passes back through said polarization rotator and its polarization is converted to a linear polarization state that is directed through said polarizing beamsplitter to said velocity-sensing interferometer.

18. A detection system for detecting displacement of a workpiece surface, comprising:

an optical beam generator which generates an optical probe beam and which is arranged so that said probe beam is reflected from said surface and phase modulated by said displacement;

a velocity-sensing interferometer positioned to receive said reflected and phase-modulated probe beam and configured to generate, in response, interferometer beams that converge at a non-zero angle to form optical interference fringes which have a fringe motion in accordance with the velocity of said surface;

a fringe processing unit positioned to receive said interference fringes and configured to generate, in response, an output signal which corresponds to said fringe motion when the frequency of said fringe motion exceeds a predetermined threshold, and wherein said fringe processing unit comprises a non-steady-state photo-electromotive-force (NSS-photo-EMF) detector; and a processor configured to extract information about said displacement from said output signal.

19. The detection system of claim 18, wherein said NSS-photo-EMF detector comprises a photoconductive material composed of GaAs:Cr, $Bi_{12}SiO_{20}$, CdTe:V, or InP:Fe.

20. A method of detecting displacement of a workpiece surface, comprising the steps of:

reflecting an optical probe beam from said surface so that said probe beam is phase modulated by said displacement, optically interfering said phase modulated probe beam with a time-delayed portion of itself;

converging said phase modulated probe beam and said time-delayed portion at a non-zero angle to generate optical interference fringes that have a fringe motion in accordance with the velocity of said surface portion, and generating a detector signal which corresponds to said fringe motion when the frequency of said fringe motion exceeds a predetermined threshold value, wherein said generating step includes the step of detecting said interference fringes with a non-steady-state photo-electromotive-force (NSS-photo-EMF) detector.

21. The method of claim 20, wherein said interfering step includes the steps of:

dividing said phase modulated probe beam into first and second interferometer beams, and directing said interferometer beams to said NSS-photo-EMF detector so that they overlap and optically interfere at said detector, said beams directed so that their arrival times at said detector differ by an amount $\Delta t$, thereby causing the phases of said interferometer beams to differ by an amount $\phi_D$ at said detector.

22. A detection system for detecting displacement of a workpiece surface, comprising:

an optical beam generator which generates an optical probe beam and which is arranged so that said probe beam is reflected from said surface and phase modulated by said displacement;

a velocity-sensing interferometer positioned to receive said reflected and phase-modulated probe beam and configured to generate, in response, interferometer beams that converge at a non-zero angle to form optical interference fringes which have a fringe motion in accordance with the velocity of said surface, wherein said velocity sensing interferometer includes:

a beam divider which divides said reflected and phase-modulated probe beam into first and second interferometer beams;

a multimode optical fiber which receives said second interferometer beam, depolarizes said second interferometer beam and delays said second interferometer beam by a delay time $\Delta t$;

a polarizing beamsplitter which divides said second interferometer beam into a first polarized interferometer beam and a second polarized interferometer beam whose polarization is substantially orthogonal to the polarization of said first polarized interferometer beam; and a polarization rotator which rotates the polarization of said second polarized interferometer beam to be substantially aligned with the polarization of said first polarized interferometer beam;

said velocity sensing interferometer arranged to direct said first and second polarized interferometer beams to spatially separated areas of said fringe processing unit and further arranged to direct said first interferometer beam to substantially overlap said spatially separated areas and converge at a non-zero angle with said first and second polarized interferometer beams to form said optical interference fringes, and a fringe processing unit positioned to receive said interference fringes and configured to generate, in response, an output signal which corresponds to said fringe motion when the frequency of said fringe motion exceeds a predetermined threshold.

23. The detection system of claim 22, wherein said polarizing beamsplitter is arranged to substantially align the polarization of said first polarized interferometer beam with the polarization of said first interferometer beam.

24. A detection system for detecting displacement of a workpiece surface, comprising:

an optical beam generator which generates an optical probe beam and which is arranged so that said probe beam is reflected from said surface and phase modulated by said displacement, a velocity-sensing interferometer positioned to receive said reflected and phase-modulated probe beam and configured to generate, in response, interferometer beams that converge at a non-zero angle to form optical interference fringes which have a fringe motion in accordance with the velocity of said surface, wherein said velocity sensing interferometer includes:

a beam divider which divides said reflected and phase-modulated probe beam into first and second interferometer beams;

a multimode optical fiber which receives said second interferometer beam, depolarizes said second interferometer beam and delays said second interferometer beam by a delay time $\Delta t$;

a polarizing beamsplitter which divides said second interferometer beam into a first polarized interferometer beam and a second polarized interferometer beam whose polarization is substantially orthogonal to the polarization of said first polarized interferometer beam; and a polarization rotator which rotates the polarization of said second polarized interferometer beam to be substantially aligned with the polarization of said first polarized interferometer beam;

said velocity sensing interferometer arranged to direct said first and second polarized interferometer beams to spatially separated areas of said fringe processing unit and further arranged to direct said first interferometer beam to substantially overlap said spatially separated areas and converge at a non-zero angle with said first and second polarized interferometer beams to form said optical interference fringes, a fringe processing unit positioned to receive said interference fringes and configured to generate, in response, an output signal which corresponds to said fringe motion when the frequency of said fringe motion exceeds a predetermined threshold; and a processor configured to extract information about said displacement from said output signal.

25. The detection system of claim 24, wherein said polarizing beamsplitter is arranged to substantially align the polarization of said first polarized interferometer beam with the polarization of said first interferometer beam.

* * * * *